(12) United States Patent
Kim et al.

(10) Patent No.: US 7,892,415 B2
(45) Date of Patent: Feb. 22, 2011

(54) MESOPOROUS PLATINUM ELECTRODE AND METHOD FOR DETECTING BIOCHEMICAL SUBSTRATE USING THE MESOPOROUS PLATINUM ELECTRODE

(75) Inventors: Hee-Chan Kim, Seoul (KR); Sejin Park, Seoul (KR); Taek-Dong Chung, Seoul (KR)

(73) Assignee: Cubiq, Inc, Palo Alto, CA (US)

( * ) Notice: Subject to any disclaimer, the term of this patent is extended or adjusted under 35 U.S.C. 154(b) by 1226 days.

(21) Appl. No.: 10/528,721

(22) PCT Filed: May 2, 2003

(86) PCT No.: PCT/KR03/00884

§ 371 (c)(1),
(2), (4) Date: Mar. 22, 2005

(87) PCT Pub. No.: WO2004/029611

PCT Pub. Date: Apr. 8, 2004

(65) Prior Publication Data

US 2006/0008667 A1    Jan. 12, 2006

(30) Foreign Application Priority Data

Sep. 24, 2002 (KR) .................. 10-2002-0057740

(51) Int. Cl.
*G01N 27/26* (2006.01)
(52) U.S. Cl. .................. 205/792; 204/290.14; 205/67
(58) Field of Classification Search .................. 205/792
See application file for complete search history.

(56) References Cited

U.S. PATENT DOCUMENTS

| 4,127,448 | A * | 11/1978 | Schick et al. | ............ 205/777.5 |
| 6,203,925 | B1 * | 3/2001 | Attard et al. | ................. 428/613 |
| 6,503,382 | B1 * | 1/2003 | Bartlett et al. | ................. 205/67 |

FOREIGN PATENT DOCUMENTS

| JP | 09 318587 | 12/1997 |
| JP | 2002 250713 | 6/2002 |
| KR | 2001110272 | 12/2001 |
| WO | WO 9900536 A2 * | 1/1999 |

OTHER PUBLICATIONS

Nomenclature of Structural and Compositional Characteristics of Ordered Microporous and Mesoporous Materials with Inorganic Hosts, L.B. McCusker et al., Pure & Appl. Chem., vol. 73, No. 2, 381-394, 382 (2001).*
Recommendations for the Characterization of Porous Solids, J. Rouquerol et al., Pure & Appl. Chem., vol. 66, No. 8, 1739-1758, 1745 (1994).*
Electrochemical Glucose Oxidation on a Platinized Platinum Electrode in Krebs-Ringer Solution, Marincic et al., J. Electrochem. Soc.: Electrochemical Science and Technology 126 (1), 43-49 (1979).*
Detection of Hydrogen Peroxide at Mesoporous Platinum Microelectrodes, Evans et al., Anal. Chem. 74, 1322-1326 (2002).*
Chemical Sensors and Biosensors, Brian R. Eggins, John Wiley & Sons, 16-18 (2002).*
Platinum Microelectrodes with Unique High Surface Areas, Elliott et al., Langmuir 15 (22), 7411-7415 (1999).*
Electrochemical Glucose Oxidation on a Platinized Electrode in Krebs-Ringer Solution, Marincic et al., J. Electrochem. Soc.: Electrochemical Science and Technology 126 (10), 1687-1692 (1979).*
Electrochemical Oxidation of Nucleic Acids and Proteins at Graphite Electrode: Qualitative Aspects, Brabec V., J. of Electroanal. Chem. 116, 69-82 (1980).*

* cited by examiner

*Primary Examiner*—Harry D Wilkins, III
*Assistant Examiner*—Bryan D. Ripa
(74) *Attorney, Agent, or Firm*—Thomas Chan

(57) ABSTRACT

The present invention relates to a mesoporous platinum electrode for detecting biochemical substrate, comprising an electrode and a mesoporous platinum layer covering the surface thereof, and a method for detecting a biochemical substrate using the mesoporous platinum electrode. Using the present invention, glucose concentration can be selectively determined while excluding interference of interfering agents.

8 Claims, 2 Drawing Sheets

MESOPOROUS PLATINUM ELECTRODE AND METHOD FOR DETECTING BIOCHEMICAL SUBSTRATE USING THE MESOPOROUS PLATINUM ELECTRODE

BACKGROUND OF THE INVENTION (a) Field of the Invention

The present invention relates to a mesoporous platinum electrode and a method for detecting a biochemical substrate using it, and more particularly to a mesoporous platinum electrode including an electrode with a mesoporous platinum layer covering a surface thereof, and a method for quantify the concentration of -glucose by detecting a selective response to the glucose oxidation reaction using the mesoporous platinum electrode.

(b) Description of the Related Art

A biosensor, in combination with electric devices, converts chemical information in a biological sample into an electrical signal, which can be easily treated. Biosensors are widely developed and applied in the medical field, due to the advantages of real-time selective monitoring of quantitative information of an analyte without complicated chemical and biological pre-treatments.

The study of biosensors for glucose has been extensively carried out for the purpose of glucose concentration monitoring for diabetes. The biosensor for glucose detection measures the concentration of glucose (analyte) using the enzyme layer that is immobilized in the confined region, generally on an electrode. Enzymatic glucose biosensors using enzyme have been studied extensively and developed in various types. However, there has been limited application because of enzyme instability. The temperature and pH affect severely on the activity of enzyme.

The studies on non-enzymatic biosensors for glucose detection have been carried out (Vassilyev, Y. B., Khazova, O. A., Nikolaeva, N. N. J. Electroanal. Chem. 1985, 196, 105; Beden, B., Largeaud, F., Kokoh, K. B., Lamy, C. Anal. Chem. 1996, 41, 701; Bae, I. T., Yeager, E., Xing, X., Liu, C. C. J. Electroanal. Chem. 1991, 309, 131; Sakamoto, M., Takamura, K. Bioelectrochem. Bioener. 1982, 9, 571; Kokkinidis, G., Xonoglou, N. Bioelectrochem. Bioener. 1985, 14, 375; Wittstock, G., Strubing, A., Szargan, R., Werner, G. J. Electroanal. Chem. 1998, 444, 61-73; Zhang, X., Chan, K.-Y., You, J.-K., Lin, Z.-G., Tseung, A. C. C. J. Electroanal. Chem. 1997, 430, 147-153; Sun, Y., Buck, H., Mallouk, T. E. Anal. Chem. 2001, 73, 1599-1604; Shoji, E., Freund, M. S. 2001, 123, 3383-3384). However, most of the non-enzymatic glucose sensors studied undergo interference by ascorbic acid (AA), uric acid, and 4-acetamidophenol (AP), which are important interfering species.

An example of a non-enzymatic glucose biosensor is one that utilizes the direct oxidation of glucose on a platinum surface (Anal. Chem. 2001, 73, 1599-1604). In the direct oxidation on the platinum electrode, the oxidation rate of glucose is much lower than that of interfering species, so it is very difficult to construct a non-enzymatic amperometric sensor using platinum on an electrode.

A possible method to alleviate the problems met by platinum is to use a Pt-Pb alloy electrode ($Pt_2Pb$ electrodes). Compared with pure platinum surfaces, glucose is electrochemically oxidized on $Pt_2Pb$ surfaces at remarkably negative potentials, and $Pt_2Pb$ is relatively insensitive to interfering species such as L-ascorbic acid (AA), uric acid, 4-acetamidophenol (AP), and so on. Moreover, $Pt_2Pb$ operates more stably due to insoluble Pb and larger responses than pure Pt. However, in spite of these valuable advantages, surface poisoning by chloride ions remains a serious problem, in which the amperometric signal diminishes rapidly in the presence of 0.01 N NaCl and eventually almost disappears.

The modification of platinum surfaces with other materials has also been attempted. Even though platinum surfaces modified by Tl, Pb, Bi, or $WO_3$ reportedly show catalytic activity for glucose oxidation, the dissolution of metal ions and the toxicity of the heavy metal elements involved prevent these methods from being put to practical use.

Mesoporous materials have a pore size between 2 and 50 nm, and a micell structure or a liquid crystal structure consisting of surfactants induces the pore structure of the mesoporous materials. The surfactants consist of a hydrophilic head group and a hydrophobic tail group, and various self-assembled micell and liquid crystal structures are comprised of the surfactants in aqueous solution. Organic/inorganic nanocomposites are formed by interaction between the hydrophilic group of the surface of the micell or liquid crystal structure and the inorganic material, and mesoporous materials are obtained by extraction of surfactants. Mesoporous platinum was fabricated by this principle, and studies on characteristics thereof have been performed (e.g. Gollas, B., Elliott, J. M., Bartlett, P. N. Electrochimica Acta 2000, 45, 3711-3724; Attard, G. S., Glyde, J. C., Goeltner, C. G. Nature 1995, 378, 366-368; Attard, G. S., Goeltner, C. G., Corker, J. M., Henke, S., Templer, R. H. Angew. Chem. Int. Ed. 1997, 36, 1315; Whitehead, A. H., Elliott, J. M., Owen, J. R., Attard, G. S. Chem. Commun. 1999, 331-332; Attard, G. S., Edgar, M., Goeltner, C. G. Acta Mater. 1998, 46, 751-758; Birkin, P. R., Elliott, J. M., Watson, Y. E. Chem. Commun. 2000, 1693-1694; Elliott, J. M., Owen, J. R. Phys. Chem. Chem. Phys. 2000, 2, 5653-5659). Mesoporous platinum film was initially produced by electrodeposition from a hexagonal ($H_1$) liquid crystalline phase composed of the non-ionic surfactant (octaethylene glycol monohexadecyl ether, $C_{16}EO_8$) (e.g. Attard, G. S., Bartlett, P. N., Coleman, N. R. B., Elliott, J. M., Owen, J. R., Wang, J. H. Science 1997, 278, 838-840). Reportedly, the electrodeposited platinum film with cylindrical hexagonally arrayed pores (pore diameter, 2.5 nm; pore-pore distance, 5.0 nm) was adherent and shiny. According to Evans et al. (Evans, S. A. G., Elliott, J. M., Andrews, L. M., Bartlett, P. N., Doyle, P. J., Denuault, G. Anal. Chem. 2002, 74, 1322-1326), mesoporous Pt films (Elliott, J. M., Birkin, P. R., Bartlett, P. N., Attard, G. S. Langmuir 1999, 15, 7411-7415) electrodeposited onto microelectrodes showed tremendous improvements in hydrogen peroxide detection sensitivity compared with bare platinum.

SUMMARY OF THE INVENTION

In order to alleviate the drawbacks of previous technology, and it is an object of the present invention to provide a non-enzymatic and heavy-metal-free detection method for glucose.

It is another object of the present invention to provide a non-enzymatic method of selectively detecting glucose oxidation using mesoporous platinum.

To accomplish the objects mentioned above, the present invention provides a mesoporous platinum electrode for detecting biochemical substrate, comprising an electrode and a mesoporous platinum layer covering the surface thereof.

The present invention provides a method for detecting a biochemical substrate comprising (a) obtaining a mesoporous platinum electrode including a electrode with a mesoporous platinum layer covering a surface thereof, (b) contacting a sample solution expected to contain the biochemical substrate with the mesoporous platinum electrode, (c) detecting a response current generated by applying a voltage to the mesoporous platinum electrode.

DETAILED DESCRIPTION OF THE PREFERRED EMBODIMENTS

Figure 1:
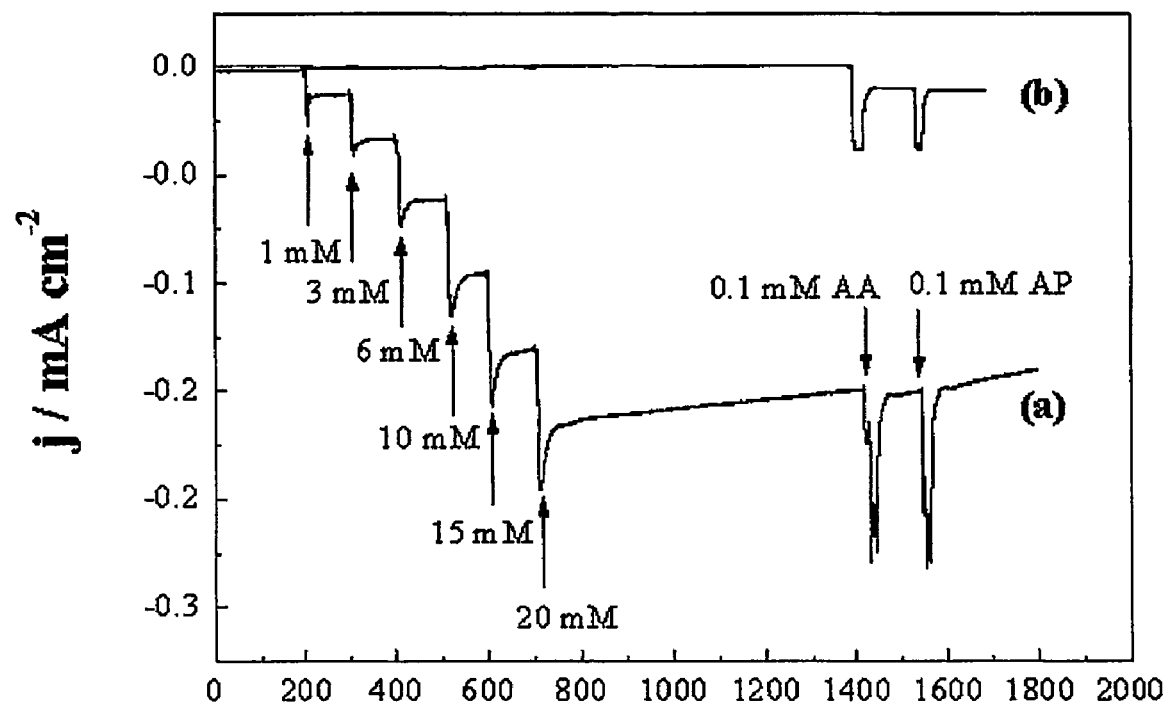
FIG. 1 shows the generated response current value when glucose, ascorbic acid, and acetamidophenol respectively is contacted with the mesoporous platinum electrode.

The present invention is related to a method of detecting a biochemical substrate using a non-enzymatic biosensor, and more particularly, to a method of quantitating glucose concentration by monitoring the oxidation of glucose with a mesoporous platinum electrode. Examples of the biochemical substrate include glucose, other saccharides (galactose, fructose, lactose, maltose, sucrose, etc.), electrochemically active proteins (containing redox active group like hemin, Cu(II), FeS, flavin mononucleotide, flavin adenine dinucleotide, and disulfie), and amino acids (like Tyr and Trp).

The biosensor of the present invention includes a mesoporous platinum electrode that comprises an electrode and a mesoporous Pt layer covering the surface thereof. The biosensor can further contain a means that provides a potential to the electrode, or a means that can detect an amperometric response of the electrode.

The electrode can be a noble metal such as carbon, platinum, gold, or silver, or a metal resistive to acid such as stainless steel.

The roughness of mesoporous Pt electrodes is smaller than the scale of the chronoamperometric diffusion field in most cases. Since the diffusion layers reach several micrometers from the electrode surface in milliseconds, reactants inside the mesopores (of 2-50 nm in diameter) are depleted in diffusion-controlled electrochemical systems. As a result, for rapidly oxidizable and/or reducible reactants, the faradaic current is just proportional to the apparent geometric area of the electrode within milliseconds regardless of the mesoporous roughness after a potential step. On the other hand, faradaic current associated with kinetic-controlled electrochemical events is sensitive to the nanoscopic area of the electrode rather than its geometric area. Thus, the mesoporous platinum electrode can be used to selectively enhance the faradaic current from a sluggish reaction.

The mesoporous platinum layer can be fabricated by various methods according to the known mesoporous material preparation method, and preferably it can be fabricated by electrodeposition from a hexagonal liquid crystal phase comprising a non-ionic surfactant (octaethylene glycol monohexadecyl ether, $C_{16}EO_8$). The electrodeposited mesoporous Pt layer is formed uniformly on the metal electrode.

The mesoporous platinum layer has pores with diameters of 2-50 nm. It is desirable that the roughness factor (the ratio of real surface area to geometric area) is as large as possible to enhance the selectivity and sensitivity for glucose. Practically the thickness of the layer is 20-5000 nm. If the thickness is less than 20 nm, a mesoporous structure is not sufficiently formed and the selectivity for glucose can be poor. If the thickness is more than 5000 nm, pores can be blocked during the growth of the mesoporous Pt. The size of pores and thickness of the wall between pores is regulated by the length of hydrophobic and hydrophilic chains, so it is important to use adequate surfactant.

The method for detecting a biochemical substrate of the present invention comprises:

(a) obtaining a mesoporous platinum electrode including a electrode with a mesoporous platinum layer covering a surface thereof;

(b) contacting a sample solution expected to contain the biochemical substrate with the mesoporous platinum electrode; and (c) detecting a response current generated by applying a voltage to the mesoporous platinum electrode.

The sample solution can be all kinds of body fluids from humans or animals, and it can further contain a phosphate buffered solution (pH 7.4) containing NaCl. The biochemical substrate can be measured in a sample of water, blood, urine, serum or PBS buffer.

The adequate range of the applying voltage is preferably between −0.1 and 0.5 V vs. a reference electrode. If the potential is outside this range, it may be difficult to measure the glucose concentration because other electrochemical processes such as adsorption/desorption of protons, formation of a platinum oxide layer, and oxygen reduction may occur significantly. The reference electrode prefers Ag/AgCl.

The current produced is proportional to biochemical substrate present in the sample from a range of about 0 to 200 mM.

In one embodiment, the mesoporous platinum electrode of the present invention shows a linear response to glucose concentration (FIGS. 1 and 2), and it shows a very low sensitivity to interfering materials. That is, the mesoporous platinum electrode can selectively respond to the glucose oxidation reaction.

The mesoporous surface of platinum offers a few attractive features that have not been shown in any earlier studies. Firstly, it shows non-enzymatic selectivity over representative interfering species. Although Sun et al.(Sun,Y.; Buck, H.; Mallouk, T. E. Anal. Chem. 2001, 73, 1599-1604.) reported the $Pt_2Pb$ alloy electrode insensitive to interfering materials, it was achieved simply by lowering potential where the interfering materials are not oxidized. Therefore, the mesoporous platinum electrode of the present invention is more effective because selectivity for glucose is evaluated at a potential that allows the oxidation of the interfering material. Considering physiological level of glucose (3-8 mM) and interfering agents (0.1 mM), mesoporous platinum electrode retains sufficient selectivity for clinical application, even without enzyme or additional outer membrane.

Secondly, the function of the mesoporous surface is almost free from deterioration in the presence of chloride ion, even in the PBS level (0.15 M). Most of electrochemical sensors based on novel metals for non-enzymatic glucose detection lose almost entire activity by poisoning by blocking materials, especially chloride ion. Concerning the high concentration of chloride ion in physiological fluids, the excellent performance of this simple system encourages us to find new breakthrough toward enzyme-free chemical sensors.

Finally, mesoporous platinum electrode is mechanically and chemically stable, and its surface can be easily regenerated by electrochemical cleaning. It is expected that mesoporous platinum electrode can be embedded inside the microchannels on sophisticatedly engineered chips to combine with microfluidics.

Examples of the present invention are demonstrated below. The examples below are to illustrate the invention, and the present invention is not limited by the examples.

EXAMPLE 1

Fabrication of Mesoporous Pt Electrode $C_{16}EO_8$ (0.42 g), distilled water (0.29 g), and hydrogen hexachloroplatinate hydrate (0.29 g) were mixed, and the temperature was raised to 80° C. until the mixture became transparent and homogeneous. Pt electrodes were inserted into the homogeneous mixture, and the temperature was lowered to room temperature (~23-26° C.). At this stage the mixture became a highly viscous liquid crystalline phase. Platinum deposition was carried out on a polished platinum rod electrode at a constant potential (−0.06 V vs. Ag/AgCl). The resulting mesoporous Pt electrode was placed in distilled water for 1 hr to extract $C_{16}EO_8$. After the extraction was repeated 3-4 times, electrochemical cleaning was performed using a cycling potential between +1 and −0.45 V versus Ag/AgCl in 0.5 N sulfuric acid until reproducibly identical cyclic voltammograms were obtained.

The prepared mesoporous Pt electrode had a hexagonally arranged pore structure with a diameter of 2.5 nm and a wall thickness of 2.5 nm. The characteristics of the mesoporous Pt were determined as follows.

Roughness factor of 72.5
  Specific area, of 37 $m^2/g$ with roughness factor of 72, assuming ~30% of faradaic efficiency during electrodeposition process.
  Mirror-like surface attributed to its excellent flatness reported to be 20+5 nm over a $mm^2$ area of a 300 nm thick film
  Single X-ray diffraction peak at 1.68 Å (2θ) corresponding to a pore-pore distance of 6.1 nm
  Diffusion characteristics same as those of a well-polished Pt (Pt-s) surface

EXAMPLE 2

Quantitation of Glucose Concentration using Mesoporous Pt Electrode

A current was measured using the mesoporous Pt electrode immersed in a phosphate buffered saline solution (0.1 M phosphate, 0.15 M NaCl, pH 7.4, 37.2±0.2° C.) at 0.4 V vs Ag/AgCl as glucose, ascorbic acid, and acetamidophenol were added. The same measurement was done using polished smooth Pt as a control.

FIG. 1 shows current density vs time curves of responses of (a) mesoporous Pt electrode (roughness factor, 72) and (b) Pt-s (roughness factor, 2.6) to glucose, ascorbic acid (AA), and acetamidophenol (AP) at +0.4 V vs Ag/AgCl in aerated PBS (pH 7.4, 37.2±0.2° C.). Glucose, ascorbic acid, and acetamidophenol were added at the points indicated by arrows to the concentrations mentioned.

In amperometric responses of the mesoporous Pt electrode to glucose; AA and AP in phosphate buffered saline (PBS) solution containing 0.1 M phosphated and 0.15 M NaCl (pH 7.4, 37.2±0.2° C.), the mesoporous Pt electrode responds to glucose sensitively whereas Pt-s shows almost no signal in the range of 1-20 mM. In addition, the mesoporous Pt selectively detected glucose rather than other interfering materials such as ascorbic acid and acetamidophenol. On the other hand, sensitivity for glucose was very low in comparison with the interfering species on smooth Pt.

Figure 2:
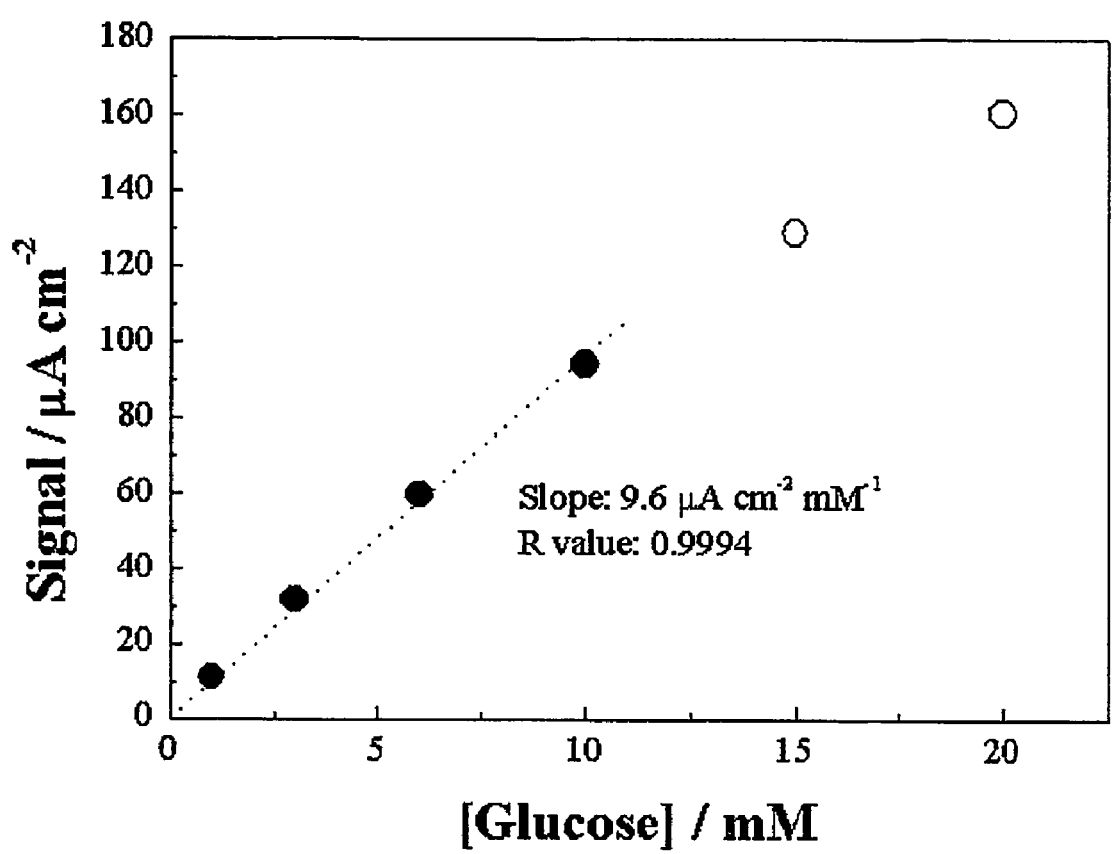
FIG. 2 is the calibration curve showing current generated relative to glucose concentration in the mesoporous platinum electrode.

FIG. 2 is a calibration curve showing the response relative to glucose concentration on the mesoporous Pt electrode. The signals were determined in quiescent solution 100 s after glucose was added to the solution during stirring.

Table 1 shows the responses of mesoporous Pt and smooth Pt to glucose and interfering materials.

TABLE 1

| Electrode | Glucose[a] | Ascorbic acid[b] | Acetamidophenol[b] |
|---|---|---|---|
| Mesoporous Pt | 9.6 | 4.4 | 1.1 |
| Smooth Pt | 0.039 | 10 | 0.75 |

[a]Sensitivity ($\mu A\,cm^{-2}\,mM^{-1}$) for glucose.
[b]Signals for 0.1 mM ($\mu A\,cm^{-2}$).

In FIG. 2 and Table 1, the mesoporous Pt electrode shows sensitivity of 9.6 $\mu Acm^{-2}mM^{-1}$, and the smooth Pt shows 0.039 $\mu Acm^{-2}mM^{-1}$, in the glucose concentration range of 0-10 mM. Thus, the mesoporous Pt enhanced the sensitivity for glucose by 250 times that of the smooth Pt. The glucose concentration in a sample can be calculated using the calibration curve in FIG. 2.

As mentioned above, a mesoporous platinum electrode including an electrode and a mesoporous platinum layer covering the surface thereof of the present invention can be applied to measure the glucose concentration quantitatively, and selective detection for glucose can be realized because the mesoporous platinum excludes interference by interfering species. Furthermore, application of the mesoporous platinum as non-enzymatic glucose sensor largely enhances the selectivity, sensitivity, and stability in comparison with the previous glucose sensors.

What is claimed is:

1. A method for detecting glucose comprising: obtaining a mesoporous platinum electrode in which the mesoporous platinum electrode comprises an electrode and a mesoporous platinum layer covering the surface thereof and in which the mesoporous platinum electrode is a non-enzymatic electrode without any enzyme immobilized thereon that reacts with the glucose to produce an electrical signal; contacting a sample solution expected to contain the biochemical substrate with the mesoporous platinum electrode; detecting a response current generated by applying a voltage to the mesoporous platinum electrode.

2. The method of claim 1, wherein the electrode is a noble metal or an acid-resistive metal.

3. The method of claim 1, wherein the electrode is selected from the group consisting of carbon, platinum, gold, silver, and stainless steel.

4. The method of claim 1, wherein the mesoporous platinum layer has a thickness of 20-5000 nm.

5. The method of claim 1, wherein the current is measured amperometrically.

6. The method of claim 1, wherein a range of the applying voltage is between −0.1 and 0.5 V vs. a reference electrode.

7. The method of claim 6, wherein the reference electrode is Ag/AgCl.

8. The method of claim 1, wherein the current generated is proportional to the glucose present in the sample from a range of 0 to 20 mM glucose.

* * * * *